United States Patent [19]

Perdoncin et al.

[11] Patent Number: 5,023,381

[45] Date of Patent: Jun. 11, 1991

[54] PROCESS FOR PREPARING AN ORGANIC SYNTHESIS INTERMEDIATE

[75] Inventors: Giulio Perdoncin, Vicenza; Claudio Giordano, Monza; Maurizio Paiocchi, Milan; Roberto Casagrande, Bresso, all of Italy

[73] Assignee: Zambon Group S.p.A., Vicenza, Italy

[21] Appl. No.: 454,001

[22] Filed: Dec. 20, 1989

[30] Foreign Application Priority Data

Dec. 22, 1988 [IT] Italy ................................ 23053 A/88

[51] Int. Cl.[5] .............................................. C07C 45/45
[52] U.S. Cl. .................................................... 568/322
[58] Field of Search ........................ 568/315, 322, 310

[56] References Cited

U.S. PATENT DOCUMENTS

| | | | |
|---|---|---|---|
| 3,803,245 | 4/1974 | Lodewijk | 568/328 |
| 4,593,125 | 6/1986 | Davenport et al. | 568/322 |
| 4,736,061 | 4/1988 | Piccolo et al. | 568/315 |
| 4,868,338 | 9/1989 | Magni et al. | 568/322 |

*Primary Examiner*—James H. Reamer
*Attorney, Agent, or Firm*—Birch, Stewart, Kolasch & Birch

[57] ABSTRACT

A process is described for the preparation of 2-methoxy-6-propionyl-naphthalene, an intermediate in the synthesis of naproxen.

The process consists of Friedel-Crafts acylation of 2-methoxy-naphthalene, and obviates the drawbacks related to the use of nitrobenzene as solvent.

3 Claims, No Drawings

PROCESS FOR PREPARING AN ORGANIC SYNTHESIS INTERMEDIATE

This invention relates to a process for preparing 2-methoxy-6-propionly-naphthalene, an intermediate useful in organic synthesis.

Said compound, already known for many years, is used in the synthesis of 2(R, S)-2-(6-methoxy-2-naphthyl)-propionic acid, from which the S enantiomer, an anti-inflammatory and analgesic drug known as naproxen, is separated by resolution.

Recently, 2-methoxy-6-propionyl-naphthalene has been used as the starting substance in the asymmetric synthesis of naproxen (European patent No. 158,913, Zambon S.p.A.).

2-methoxy-6-propionyl-naphthalene is normally prepared industrially by Friedel-Crafts acylation of 2-methoxy-naphthalene with propionyl chloride in the presence of a Lewis acid, preferably $AlCl_3$.

Said reaction is conducted by totally conventional methods, using a substantially equimolar ratio of aromatic substrate to acylating substrate or a slight excess of this latter, as is normal in Friedel-Crafts acylation.

In accordance with the practice gained over very many years, the catalyst ($AlCl_3$) is used in excess over the aromatic substrate.

The type of solvent is known to influence the reaction products.

In this respect, if 2-methoxy-naphthalene is acylated with propionyl chloride in the presence of $AlCl_3$ using nitrobenzene as solvent, the main reaction product is the sought product, i.e. 2-methoxy-6-propionyl-naphthalene.

However if the reaction is carried out in benzene, carbon disulphide or chlorinated solvents, the main reaction product is 2-methoxy-1-propionyl-naphthalene.

Consequently the preparation of 2-methoxy-6-propionyl-naphthalene by Friedel-Crafts acylation is conducted according to the literature in nitrobenzene.

This solvent, however, has serious industrial drawbacks both because of its noxious nature and the fact that, being high boiling, it requires energy-expensive procedures for its removal to isolate the reaction product, and also because when present in large quantity it is difficult to separate the aqueous/organic phases during the processing of the reaction mixture.

Two different procedures have recently been proposed for the Friedel-Crafts acylation of 2-methoxy-naphthalene.

One of these involves conducting the reaction in anhydrous hydrofluoric acid (European patent application No. 176,142, Blaschim S.p.A. and U.S. Pat. No. 4,593,125, Celanese Corp.)

Because of the considerable danger and corrosiveness of anhydrous hydrofluoric acid, this process requires special hermetically sealed plants operating in closed cycle, which means that it can only be used if suitable equipment and technology are available.

The other procedure involves conducting the acylation while maintaining the molar ratio of the naphthalene derivative to the acylating agent and of the acylating agent to the Friedel-Crafts catalyst constantly within determined limits with time (European patent application No. 282,134, Blaschim S.p.A.).

This procedure can be conducted either in nitrobenzene or in other solvents, but requires a complicated plant comprising the reactor, two premixers, an adjustable system for the feed of the reactants and catalyst into the reactor, and an automatic system for withdrawing samples from the reaction mass and analyzing them in order to periodically correct the reactant and catalyst feed to the reactor. The implementation of this process also requires exact knowledge of the reactant concentrations and any variations in time therewith. In this respect, propionyl chloride contains variable quantities of propionic acid, and commercial aluminum chloride is of variable purity which is different to determine.

It is also unclear how the ratios can be maintained constant during the course of the reaction, which is not free of by-products which selectively consume one of the two reactants and the catalyst.

There is therefore still a considerable need for a simple process for preparing 2-methoxy-6-propionyl-naphthalene without having to use very large quantities of nitrobenzene or special plants for the use of anhydrous hydrofluoric acid, or complicated systems for continuous sampling and analysis, with the consequent variation in the flow of the reactants and catalyst through the reactor.

We have now found that in preparing 2-methoxy-6-propionyl-naphthalene from 2-methoxy-naphthalene and propionyl chloride in various solvents and using various types of catalyst, 2-methoxy-1-propionyl-naphthalene is initially obtained as the main reaction product, but that this evolves to 2-methoxy-6-propionyl-naphthalene by equilibration catalyzed by an $AlCl_3$-nitrobenzene complex.

This result, which is totally unexpected on the basis of the literature, enables an industrial process to be implemented for preparing 2-methoxy-6-propionyl-naphthalene from 2-methoxy-naphthalene and propionyl chloride using only a small nitrobenzene quantity.

This process, to which the present invention relates, consists of using an inert solvent other than nitrobenzene, for example a chlorinated hydrocarbon, and $AlCl_3$ as catalyst in moderate excess over the propionyl chloride, and specifically a quantity of between 1.1 and 2 moles of $AlCl_3$ per mole of propionyl chloride, plus only a small quantity of nitrobenzene substantially equivalent in moles to the excess of $AlCl_3$.

The process does not require special plant, as the normal equipment for the Friedel-Crafts reaction can be used, the results obtained being unexpectedly substantially identical to those normally obtained when using nitrobenzene as solvent.

Examples of chlorinated solvents suitable for the reaction are 1,2-dichloroethane, chlorobenzene, dichlorobenzene and methylene chloride, this latter being preferred.

The aforesaid nitrobenzene quantity, i.e. substantially equivalent in moles to the excess of $AlCl_3$, is sufficient to obtain results identical to those obtained when the reaction is conducted in nitrobenzene as solvent.

Larger quantities do not improve the result, the aforesaid range being the optimum.

It is apparent to the expert of the art that the quantity of nitrobenzene used in the process according to the present invention is much less than that which would be used if the nitrobenzene itself was the reaction solvent.

This fact, besides representing a significant reduction in the use of a dangerous solvent, allows much simpler processing of the mixture at the end of the reaction.

The reaction temperature is not critical within the normal range of industrial use, the preferred range being 0°–40° C., the preferred temperature being ambient for reasons of energy saving.

The reaction time depends on the normal influencing factors. At a temperature of 20° C., the 2-methoxy-naphthalene attains a high degree of conversion (exceeding 90%) within about 6–14 hours, the conversion yield exceeding 85%.

In one embodiment, the process of the present invention is conducted by feeding the 2-methoxy-naphthalene, the organic solvent (for example $CH_2Cl_2$), and the predetermined quantities of nitrobenzene and $AlCl_3$ into the reactor at ambient temperature and pressure. The propionyl chloride is then added slowly.

The mass is poured into precooled water on termination of the reaction.

The organic phase, consisting of a solution of the desired ketone in methylene chloride and nitrobenzene, is separated and evaporated.

The residue is crystallized to obtain 2-methoxy-6-propionyl-naphthalene with high yield and purity.

The process of the present invention can also be implemented in two stages.

In the first stage, 2-methoxy-naphthalene and propionyl chloride are reacted in a solvent other than nitrobenzene, in the presence of any suitable Friedel-Crafts catalyst.

A mixture of 2-methoxy-1-propionyl-naphthalene and 2-methoxy-6-propionyl-naphthalene is obtained, which if required can be isolated.

In the second stage the mixture is treated with a catalytic quantity of $AlCl_3$ and a quantity of nitrobenzene equimolar to the $AlCl_3$.

In this manner the 2-methoxy-1-propionyl-naphthalene is converted to 2-methoxy-6-propionyl-naphthalene, which then represents the only significant product of the process.

The following examples are given to better illustrate the present invention.

EXAMPLE 1

Nitrobenzene (0.1 moles) and aluminum trichloride (56.3 g; 0.42 moles) are added to a solution of 2-methoxy-naphthalene (51 g; 0.32 moles) in methylene chloride (156 g), while maintaining the temperature at 20° C.

Propionyl chloride (32 g; 0.36 moles) is added dropwise while maintaining the temperature at 20° C.

The reaction is followed by GLC analysis.

After 24 hours 95% of the starting substance has been converted, the 2-methoxy-6-propionyl-naphthalene being formed with a yield of 90% on the converted 2-methoxy-naphthalene.

The reaction mixture is poured into water (212 g) cooled to 0° C.

The organic phase is separated and dried over anhydrous $Na_2SO_4$.

The 2-methoxy-6-propionyl-naphthalene is obtained by evaporating the solvent, after which it is crystallized from methanol to show a M.P. of 114°–115° C. an a yield of 80%.

EXAMPLE 2

The reaction of Example 1 is repeated using 0.64 moles of $AlCl_3$ and 0.32 moles of nitrobenzene, the reactant quantities being as given.

After 6 hours the crude reaction mixture already contains 84% of 2-methoxy-6-propionyl-naphthalene, which is isolated as described in Example 1.

What is claimed is:

1. A process for preparing 2-methoxy-6-propionyl-naphthalene by Friedel-Crafts acylation of 2-methoxy-naphthalene with propionyl chloride and $AlCl_3$, consisting of using a chlorinated hydrocarbon as solvent and operating in the presence of an excess of $AlCl_3$, in a quantity of between 1.1 and 2 moles per mole of propionyl chloride, and a quantitiy of nitrobenzene substantially equivalent in moles to the $AlCl_3$ excess.

2. A process as claimed in claim 1, wherein the chlorinated solvent is methylene chloride.

3. A process as claimed in claim 1, wherein the reaction is conducted at ambient temperature.

* * * * *